(12) United States Patent
Matheny

(10) Patent No.: US 11,865,226 B2
(45) Date of Patent: Jan. 9, 2024

(54) CARDIOVASCULAR PROSTHESES

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 667 days.

(21) Appl. No.: 17/089,888

(22) Filed: Nov. 5, 2020

(65) Prior Publication Data

US 2021/0046216 A1     Feb. 18, 2021

Related U.S. Application Data

(60) Continuation of application No. 16/531,263, filed on Aug. 5, 2019, now abandoned, and a continuation of application No. 15/877,586, filed on Jan. 23, 2018, now Pat. No. 10,383,977, and a division of application No. 15/386,640, filed on Dec. 21, 2016, now Pat. No. 10,143,778, and a continuation-in-part of application No. 13/328,287, filed on Dec. 16, 2011, now Pat. No. 9,532,943.

(51) Int. Cl.
| | |
|---|---|
| *A61L 27/36* | (2006.01) |
| *A61F 2/00* | (2006.01) |
| *A61K 31/4418* | (2006.01) |
| *A61L 27/34* | (2006.01) |
| *A61L 27/38* | (2006.01) |
| *A61L 27/54* | (2006.01) |
| *A61L 27/58* | (2006.01) |
| *A61F 2/06* | (2013.01) |
| *A61L 27/50* | (2006.01) |

(52) U.S. Cl.
CPC .......... *A61L 27/3633* (2013.01); *A61F 2/00* (2013.01); *A61F 2/0095* (2013.01); *A61F 2/06* (2013.01); *A61K 31/4418* (2013.01); *A61L 27/34* (2013.01); *A61L 27/3834* (2013.01); *A61L 27/507* (2013.01); *A61L 27/54* (2013.01); *A61L 27/58* (2013.01); *A61F 2210/0004* (2013.01); *A61F 2250/0067* (2013.01); *A61L 2300/414* (2013.01); *A61L 2430/20* (2013.01)

(58) Field of Classification Search
None
See application file for complete search history.

(56) References Cited

U.S. PATENT DOCUMENTS

| | | |
|---|---|---|
| 2009/0047318 A1 | 2/2009 | Ludwig et al. |
| 2010/0222882 A1 | 9/2010 | Badylak et al. |
| 2015/0093353 A1 | 4/2015 | Matheny |
| 2015/0100115 A1 | 4/2015 | Matheny |

*Primary Examiner* — Kyung S Chang
(74) *Attorney, Agent, or Firm* — Thomas| Horstemeyer, LLP

(57) ABSTRACT

Cardiovascular prostheses for treating, reconstructing and replacing damaged or diseased cardiovascular tissue that include particulate structures that are formed from PGS, cerivastatin and everolimus. The particulate structures are configured to modulate inflammation of damaged cardiovascular tissue in vivo by increasing expression of Kruppel like factor 2 (KLF-2), whereby localized expression of monocyte chemoattractant protein 1 (MCP-1) and C-C chemokine receptor type 2 (CCR2) is inhibited at transcriptional and translational levels as a function of the KLF-2 modulation.

1 Claim, 11 Drawing Sheets

CARDIOVASCULAR PROSTHESES

CROSS-REFERENCES TO RELATED APPLICATIONS

This application is a continuation of U.S. application Ser. No. 16/531,263, filed on Aug. 5, 2019, which is a continuation of U.S. application Ser. No. 15/877,586, now U.S. Pat. No. 10,383,977, filed on Jan. 23, 2018, which is a division of U.S. application Ser. No. 15/386,640, now U.S. Pat. No. 10,143,778, filed on Dec. 21, 2016, which is a continuation-in-part of U.S. application Ser. No. 13/328,287, now U.S. Pat. No. 9,532,943, filed on Dec. 16, 2011, which claims the benefit of U.S. Provisional Application No. 61/425,172, filed on Dec. 20, 2010.

FIELD OF THE INVENTION

The present invention relates to methods and apparatus for treating damaged or diseased cardiovascular structures. More particularly, the present invention relates to cardiovascular prostheses for treating and/or reconstructing damaged or diseased cardiovascular structures.

BACKGROUND OF THE INVENTION

As is well known in the art, various cardiovascular prostheses are often employed to treat and reconstruct damaged or diseased cardiovascular structures and associated tissue, such as cardiovascular vessels and heart tissue. However, despite the growing sophistication of medical technology, the use of prostheses to treat or replace damaged biological tissue remains a frequent and serious problem in health care. The problem is often associated with the materials employed to construct the prostheses.

As is also well known in the art, the optimal prostheses material should be chemically inert, non-carcinogenic, capable of resisting mechanical stress, capable of being fabricated in the form required and sterilizable. Further, the material should be resistant to physical modification by tissue fluids, and not excite an inflammatory reaction, induce a state of allergy or hypersensitivity, or, in some cases, promote visceral adhesions.

Various materials and/or structures have thus been employed to construct prostheses that satisfy the aforementioned optimal characteristics. Such materials and structures include tantalum gauze, stainless mesh, Dacron®, Orlon®, Fortisan®, nylon, knitted polypropylene (e.g., Marlex®), microporous expanded-polytetrafluoroethylene (e.g., Gore-Tex®), Dacron reinforced silicone rubber (e.g., Silastlc®), polyglactin 910 (e.g., Vicryl®), polyester (e.g., Mersilene®), polyglycolic acid (e.g., Dexon®), processed sheep dermal collagen, crosslinked bovine pericardium (e.g., PeriGuard®), and preserved human dura (e.g., Lyodura®).

As discussed in detail below, although some of the noted prosthesis materials satisfy some of the aforementioned optimal characteristics, few, if any, satisfy all of the optimal characteristics.

Metallic mesh structures, e.g., stainless steel meshes, are generally inert and resistant to infection. Metallic mesh structures are, however, prone to fragmentation, which can, and in many instances will, occur after the first year of administration.

Synthetic mesh structures are easily molded and, except for nylon, retain their tensile strength in or on the body. Synthetic mesh structures are, however, typically non-resorbable and susceptible to infection.

A major problem associated with Marlex®, i.e. polypropylene, mesh structures is that with scar contracture, polypropylene mesh structures become distorted and separate from surrounding normal tissue.

A major problem associated with Gore-Tex®, i.e. polytetrafluoroethylene, mesh structures is that in a contaminated wound it does not allow for any macromolecular drainage, which limits treatment of infections.

Mammalian tissue, such as extracellular matrix (ECM), is also often employed to construct cardiovascular prostheses. Illustrative are the prostheses disclosed in U.S. Pat. Nos. 3,562,820 and 4,902,508. Further ECM prostheses (i.e. multi-sheet laminate structures) are disclosed in U.S. Pat. No. 8,808,363 and Applicant's Co-Pending application Ser. Nos. 14/031,423, 14/337,915, 14/566,155 and 14/566,306, which are incorporated by reference herein in their entirety.

Although many of the ECM based cardiovascular prostheses satisfy many of the aforementioned optimal characteristics, when the ECM graft comprises two or more sheets, i.e. a multi-sheet laminate, such as disclosed in Co-pending application Ser. No. 14/031,423, the laminate structures can, and in some instances will, delaminate.

Thus, readily available, versatile cardiovascular prostheses that are not prone to calcification, thrombosis, intimal hyperplasia and delamination would fill a substantial and growing clinical need.

It is therefore an object of the present invention to provide cardiovascular prostheses that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

It is another object of the present invention to provide cardiovascular prostheses that modulate inflammation and induce host tissue proliferation, remodeling and regeneration of new tissue and tissue structures with site-specific structural and functional properties when delivered to damaged cardiovascular tissue.

It is another object of the present invention to provide cardiovascular prostheses that are capable of administering a pharmacological agent to host tissue and, thereby produce a desired biological and/or therapeutic effect.

SUMMARY OF THE INVENTION

The present invention is directed to biodegradable cardiovascular prostheses for treating, reconstructing or replacing damaged or diseased cardiovascular structures and associated tissue.

According to the invention, the cardiovascular prostheses can comprise various structures and compositions, including, but not limited to, mesh constructs, encasement structures, coated structures and multi-sheet laminate structures.

In some embodiments of the invention, the prostheses comprise a plurality of particulate structures. In a preferred embodiment, the plurality of particulate structures comprise an ECM-mimicking composition. In a preferred embodiment, the ECM-mimicking composition comprises poly (glycerol sebacate) (PGS).

In some embodiments, the ECM-mimicking composition further comprises cerivastatin. In a preferred embodiment, the ECM-mimicking composition comprises a weight percent of cerivastatin in the range of 0.01 wt. % to 0.1 wt. %.

In some embodiments, the ECM-mimicking composition further comprises everolimus. In a preferred embodiment, the ECM-mimicking composition comprises a weight percent of everolimus in the range of 0.001 wt. % to 0.01 wt. %.

In a preferred embodiment, the prostheses are adapted to modulate inflammation of damaged cardiovascular tissue in vivo by increasing expression of Kruppel like factor 2 (KLF-2), whereby localized expression of monocyte chemoattractant protein 1 (MCP-1) and C-C chemokine receptor type 2 (CCR2) is inhibited at transcriptional and translational levels as a function of the KLF2 modulation.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
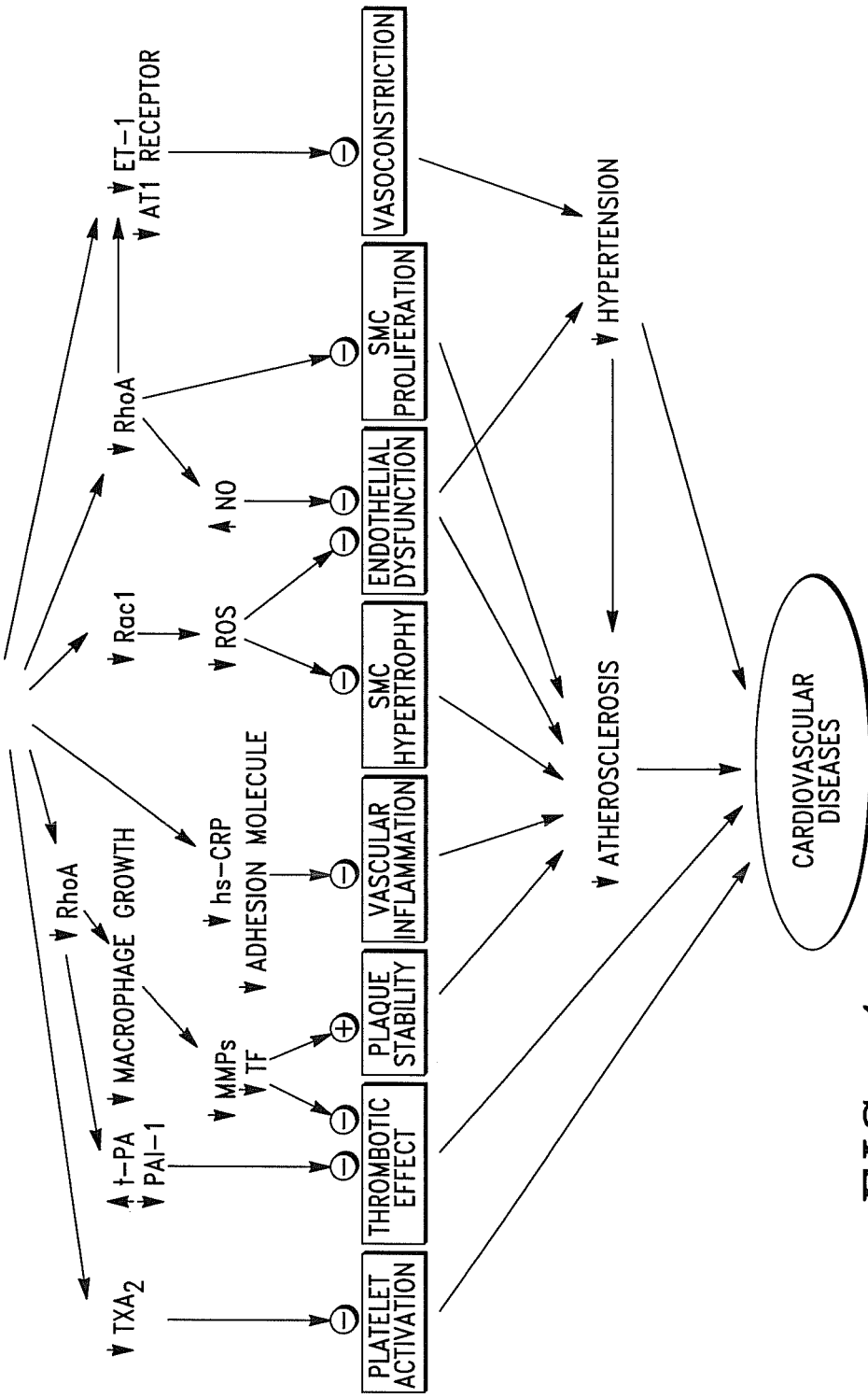
FIG. 1 is a schematic illustration showing the effects of statins on vascular cell walls, in accordance with the invention.

Before describing the present invention in detail, it is to be understood that this invention is not limited to particularly exemplified compositions, structures, apparatus, and methods, as such may, of course, vary. Thus, although a number of compositions, structures, apparatus, and methods similar or equivalent to those described herein can be used in the practice of the present invention, the preferred compositions, structures, apparatus, and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference herein in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

Definitions

The terms "extracellular matrix" and "ECM" are used interchangeably herein, and mean and include a collagen-rich substance that is found in between cells in mammalian tissue, and any material processed therefrom, e.g., acellular ECM derived from mammalian tissue sources.

According to the invention, ECM can be derived from a variety of mammalian tissue sources, including, without limitation, small intestine submucosa (SIS), urinary bladder submucosa (UBS), stomach submucosa (SS), central nervous system tissue and epithelium of mesodermal origin, i.e. mesothelial tissue.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

ECM can also be derived from basement membrane of mammalian tissue/organs, including, without limitation, urinary basement membrane (UBM), liver basement membrane (LBM), and amnion, chorion, allograft pericardium, allograft dermis, amniotic membrane, Wharton's jelly, umbilical cord, and combinations thereof.

Additional sources of mammalian basement membrane include, without limitation, spleen tissue, lymph node tissue, salivary gland tissue, prostate tissue, pancreas tissue and tissue from other secreting glands.

The ECM can also be derived from dermal tissue, subcutaneous tissue, placental tissue, cardiac tissue, e.g., pericardial and/or myocardial tissue, kidney tissue, lung tissue, gastrointestinal tissue, i.e. large and small intestinal, appendix, omentum and pancreas tissue, and combinations thereof.

ECM can also be derived from other sources, including, without limitation, collagen from plant sources and synthesized extracellular matrices, i.e. cell cultures. ECM can also comprise ECM synthesized in vitro, e.g., collagen producing cell lines, and collagen and ECM from non-mammalian tissue sources, such as, without limitation, avian, reptilian, fish, and other marine sources.

The terms "decellularized" and "acellular" are used interchangeably herein in connection with ECM, and mean and include ECM derived from mammalian tissue subjected to a decellularized process and, hence, exhibits a reduced glycosaminoglycan (GAG) content and markedly altered collagen and fibronectin structures compared to naturally occurring mammalian tissue.

The term "medical device", as used herein, means and includes a therapeutic, surgical or prosthetic device configured to modulate a biological function of a warm blooded mammal, including humans and primates; avians; domestic household or farm animals, such as cats, dogs, sheep, goats, cattle, horses and pigs; laboratory animals, such as mice, rats and guinea pigs; fish; reptiles; zoo and wild animals; and the like. The term "medical device" thus includes, without limitation, an implantable medical device, such as a pacemaker, defibrillator, synthetic heart valve, ventricular assist device, artificial heart, physiological sensor, catheter and associated components thereof, including electrical leads and lines associated therewith.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussusceptive angiogenesis, sprouting angiogenesis, therapeutic angiogenesis and vasculogenesis.

The term "adverse inflammatory response", as used herein, means and includes a physiological response that is sufficient to induce constitutive clinically relevant expression of pro-inflammatory cytokines, such as interleukin-1 beta (IL-1β) and monocyte chemoattractant protein-1 (MCP-1) in vivo.

The term "adverse biological response", as used herein, means and includes a physiological response that is sufficient to induce a biological process and/or restrict a phase associated with biological tissue healing in vivo, including without limitation, neovascularization and remodeling of the damaged biological tissue. The term "adverse biological response" thus includes an "adverse inflammatory response", e.g., development of fibrotic tissue.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors and compositions comprising same: epidermal growth factor (EGF), transforming growth factor alpha (TGF-α), transforming growth factor beta (TGF-β), basic fibroblast growth factor (bFGF) (also referred to as fibroblast growth factor-2 (FGF-2)), vascular endothelial growth factor (VEGF), hepatocyte growth factor (HGF), insulin-like growth factor (IGF), nerve growth factor (NGF), platelet derived growth factor (PDGF), tumor necrosis factor alpha (TNF-α), and placental growth factor (PLGF).

The terms "biologically active agent" and "biologically active composition" also mean and include, without limitation, the following cells and compositions comprising same: human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

The terms "biologically active agent" and "biologically active composition" also mean and include, without limitation, the following biologically active agents (referred to interchangeably herein as a "protein", "peptide" and "polypeptide") and compositions comprising same: collagen (types I-V), proteoglycans, glycosaminoglycans (GAGs), glycoproteins, growth factors, cytokines, including interleukins, e.g., IL-8 and IL-10, and interferons, cell-surface associated proteins, cell adhesion molecules (CAM), angiogenic growth factors, endothelial ligands, matrikines, cadherins, immunoglobins, fibril collagens, non-fibrillar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, osteopontins, and angiotensin converting enzymes (ACE).

The terms "biologically active agent" and "biologically active composition" also mean and include an "exosome", "microsome" or "micro-vesicle," which are used interchangeably herein, and mean and include a micellar body formed from a hydrocarbon monolayer or bilayer configured to contain or encase a composition of matter, such as a biologically active agent. The terms "exosome", "microsome" and "micro-vesicle" thus include, without limitation, a micellar body formed from a lipid layer configured to contain or encase biologically active agents and/or combinations thereof.

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-fibrotics, anti-arrhythmic agents, anti-viral agents, analgesics, steroidal anti-inflammatories, non-steroidal anti-inflammatories, antineoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscamet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF and IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antimicrobials: silver particles, copper particles, cobalt particles, nickel particles, zinc particles, zirconium particles, molybdenum particles, lead particles and mixtures thereof.

The terms "pharmacological agent", "active agent", "drug" and "active agent formulation" further mean and include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further mean and include, without limitation, the following anti-fibrotics: paclitaxel, sirolimus and derivatives thereof, including everolimus.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The term "adolescent", as used herein, means and includes a mammal that is preferably less than three (3) years of age.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

The present invention is directed to resilient, non-antigenic, biodegradable, remodelable (or bioremodelable) and, hence, biocompatible, cardiovascular prostheses that can be used to repair, augment, or replace mammalian tissues and organs.

As indicated above and discussed in detail below, in a preferred embodiment of the invention, when the cardiovascular prostheses are disposed proximate (i.e. delivered or administered to) damaged tissue, the cardiovascular prostheses induce neovascularization and/or remodeling of the damaged tissue, without inducing an adverse inflammatory response.

More preferably, when the cardiovascular prostheses are disposed proximate damaged tissue, the cardiovascular prostheses modulate inflammation of the damaged tissue and, induce neovascularization, host cell and tissue proliferation, and regeneration of new tissue and tissue structures.

The cardiovascular prostheses can thus be employed to treat various disorders, including, without limitation, atrial fibrillation (pre- and post-operative) and other causes of ventricular arrhythmias and the root causes thereof, damaged or diseased biological tissue, including, without limitation, cardiovascular tissue, e.g., infarct tissue, and damaged and diseased mammalian organs and structures, including, without limitation, cardiac vessels and valves, such as bicuspid, tricuspid and pulmonary valves, myocardium, pericardium, arteries, veins, trachea, esophagus, etc.

As indicated above, the cardiovascular prostheses can comprise various compositions and structures, including, but not limited to, particulate structures, mesh constructs, encasement structures, coated structures and multi-sheet laminate structures.

In some embodiments, the cardiovascular prostheses comprise an ECM composition comprising acellular ECM derived from a mammalian tissue source.

According to the invention, the mammalian tissue sources can comprise, without limitation, small intestine tissue, large intestine tissue, stomach tissue, lung tissue, liver tissue, kidney tissue, pancreas tissue, placental tissue, cardiac tissue, bladder tissue, prostate tissue, tissue surrounding growing enamel, tissue surrounding growing bone, and any fetal tissue from any mammalian organ.

In some embodiments of the invention, the mammalian tissue sources comprise, small intestine submucosa (SIS), urinary bladder submucosa (UBS), urinary basement membrane (UBM), liver basement membrane (LBM), stomach submucosa (SS), mesothelial tissue, placental tissue and cardiac tissue.

According to the invention, the ECM composition can comprise acellular ECM derived from one (1) mammalian tissue source or acellular ECM derived from different mammalian tissue sources.

In a preferred embodiment, the mammalian tissue source comprises an adolescent mammalian tissue source, i.e. an adolescent mammal, such as a piglet, which is preferably less than three (3) years of age.

According to the invention, an ECM material can be decellularized to provide acellular ECM by various conventional means.

According to the invention, the ECM material can be decellularized via one of the conventional decellularization methods disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

In some embodiments of the invention, the ECM material is decellularized via one of the unique Novasterilis™ processes disclosed in U.S. Pat. No. 7,108,832 and U.S. patent application Ser. No. 13/480,205; which are incorporated by reference herein in their entirety.

As stated above, in some embodiments of the invention, the ECM composition comprises at least one additional or supplemental biologically active agent or composition, i.e. an agent that induces or modulates a physiological or biological process, or cellular activity, e.g., induces proliferation, and/or growth and/or regeneration of tissue.

In a preferred embodiment of the invention, the supplemental biologically active agent is similarly derived from an adolescent mammal, i.e. a mammal less than three (3) years of age.

Suitable supplemental biologically active agents include any of the aforementioned biologically active agents, including, without limitation, the aforementioned cells and proteins.

In some embodiments, the supplemental biologically active agent comprises a growth factor, such as, without limitation, a transforming growth factor-alpha (TGF-α), transforming growth factor-beta (TGF-β), basic fibroblast growth factor (bFGF) and vascular endothelial growth factor (VEGF).

In some embodiments, the wt. % of the supplemental biologically active agent in the ECM composition (and ECM-mimicking, ECM/ECM-mimicking, and statin augmented compositions of the invention, discussed in detail below) is in the range of approximately 0.0001-20 wt. %, more preferably, in the range of approximately 0.001-1 wt. %.

In a preferred embodiment, the wt. % of the biologically active agent in the ECM composition (and ECM-mimicking, ECM/ECM-mimicking, and statin augmented compositions of the invention) is sufficient to induce or modulate a physiological or biological process, without inducing an adverse biological response, e.g., a physiological response that is sufficient to induce constitutive clinically relevant expression of pro-inflammatory cytokines.

In some embodiments, the ECM composition comprises at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-fibrotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises one of the aforementioned anti-inflammatory agents.

According to the invention, the wt. % of the pharmacological agent in the ECM composition (and ECM-mimicking, ECM/ECM-mimicking, and statin augmented compositions of the invention) is dependent on the pharmacological agent(s) employed in the composition.

By way of example, as discussed in detail below, when the pharmacological agent comprises an antibiotic, the wt. % of the antibiotic in the ECM composition (and ECM-mimicking, ECM/ECM-mimicking, and statin augmented compositions of the invention) is in the range of approximately 0.0001-20 wt. %, more preferably, in the range of approximately 0.001-1 wt. %.

In a preferred embodiment, the wt. % of the pharmacological agent in the ECM composition (and ECM-mimicking, ECM/ECM-mimicking, and statin augmented compositions of the invention) is sufficient to induce or modulate a desired biological effect in vivo, e.g., regeneration and remodeling of damaged biological tissue, without inducing an adverse biological response.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

In some embodiments, the wt. % of the HMG-CoA reductase inhibitor in the ECM composition (and ECM-mimicking, ECM/ECM-mimicking, and statin augmented compositions of the invention) is in the range of approximately 0.0001-0.2 wt. %, more preferably, in the range of approximately 0.01-0.1 wt. %.

In a preferred embodiment, the wt. % of the HMG-CoA reductase inhibitor in the ECM composition (and ECM-mimicking, ECM/ECM-mimicking, and statin augmented compositions of the invention) is similarly sufficient to induce or modulate a desired biological effect in vivo, e.g., regeneration and remodeling of damaged biological tissue, without inducing an adverse biological response.

According to the invention, when the ECM composition and, hence, cardiovascular prostheses formed therefrom, is disposed proximate damaged or diseased biological tissue, "modulated healing" is effectuated.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic, i.e. wound healing, inflammation, and their interplay with each other.

In such an instance, a minor amount of inflammation may ensue in response to tissue injury, but this level of inflammation response, e.g., platelet and/or fibrin deposition, is substantially reduced when compared to inflammation that takes place in the absence of an ECM composition of the invention.

By way of example, in some embodiments, an ECM composition (and/or ECM-mimicking composition and/or ECM/ECM-mimicking composition, discussed in detail below) and, hence, cardiovascular prosthesis formed therefrom, of the invention is specifically formulated (or designed) to alter, delay, retard, reduce, and/or detain one or more of the phases associated with healing of damaged biological tissue, including, but not limited to, the inflammatory phase (e.g., platelet or fibrin deposition), proliferative phase and maturation phase.

In some embodiments, "modulated healing" refers to the ability of an ECM composition (and/or ECM-mimicking composition and/or ECM/ECM-mimicking composition) and, hence, cardiovascular prosthesis formed therefrom, of the invention to alter a substantial inflammatory phase (e.g., platelet or fibrin deposition) at the beginning of the tissue healing process. As used herein, the phrases "alter a substantial inflammatory phase", "modulate inflammation" and "inflammation modulation" refer to the ability of an ECM composition to substantially reduce an adverse inflammatory response at an injury site and induce "wound healing", immune responses.

In some embodiments, the term "modulated healing" also refers to the ability of an ECM composition (and/or ECM-mimicking composition and/or ECM/ECM-mimicking composition) and, hence, cardiovascular prosthesis formed therefrom, of the invention to modulate inflammation of damaged biological tissue by reducing the infiltration of "acute inflammatory" M1 macrophages and increasing the migration and, hence, population of "wound healing" M2 macrophages.

In some embodiments of the invention, "modulated healing" refers to the ability of an ECM composition (and/or ECM-mimicking composition and/or ECM/ECM-mimicking composition) and, hence, cardiovascular prosthesis formed therefrom, of the invention to induce neovascularization, including vasculogenesis, angiogenesis, and intussusception, host cell and/or tissue proliferation, remodeling of damaged biological tissue, and regeneration of new tissue and tissue structures with site-specific structural and functional properties.

As indicated above, in some embodiments of the invention, an ECM composition comprises a statin, i.e. a HMG-CoA reductase inhibitor.

The most preferred statin is cerivastatin, i.e. (3R,5S,6E)-7-[4-(4-fluorophenyl)-5-(methoxymethyl)-2,6-bis(propan-2-yl)py-ridin-3-yl]-3,5-dihydroxyhept-6-enoic acid.

According to the invention, when an ECM composition (and/or and ECM/ECM-mimicking composition) comprising acellular ECM and a statin; particularly, cerivastatin (and/or an ECM-mimicking composition comprising a statin), i.e. a statin augmented composition, is disposed (i.e. delivered or administered) proximate damaged biological tissue, the statin augmented composition induces several beneficial biochemical actions or activities, which enhance modulated healing.

The beneficial biochemical actions or activities induced when a statin augmented composition is disposed to biological tissue; particularly, damaged cardiovascular tissue, are illustrated in FIG. 1.

Further details regarding the beneficial biochemical actions or activities induced when a statin augmented composition is disposed to biological tissue are set forth in U.S. Pat. No. 9,119,899, which is incorporated by reference herein in its entirety.

As discussed in detail below, one of the seminal biochemical actions or activities induced by the statin augmented composition is highly effective inflammation modulation of damaged biological tissue when the statin augmented composition is disposed proximate thereto.

As is well known in the art, damaged biological tissue undergoes inflammation-mediated repair in three phases: the inflammatory phase, proliferative phase and the maturation phase.

The inflammatory phase is an acute immune response where cytokines signal the recruitment of leukocytes, including phagocytes, e.g., M1 macrophages and dendritic cells, which clear dead endogenous or native cells. Matrix metalloproteinase (MMP) expression also signals the breakdown of endogenous ECM within the damaged biological tissue, which often occurs within ten (10) minutes after cardiovascular tissue damage.

The proliferative phase is a chronic immune response where transforming growth factor beta (TGF-β) and anti-inflammatory interleukin-10 (IL-10) suppress chemokine and inflammatory cytokine response, while promoting myofibroblast cell proliferation. The myofibroblast cells then deposit a plurality of ECM proteins, which provide a "provisional" endogenous ECM.

The maturation phase is the scarring phase where endogenous ECM proteins are crosslinked via lysyl oxidase and the myofibroblast cells subsequently enter a quiescent state. The resulting accumulation of crosslinked "provisional" ECM (or fibrotic scar tissue) often results in a disruption of the endogenous ECM network.

The "provisional" ECM lacks the anisotropic network of endogenous ECM and, hence, is structurally weaker than endogenous ECM. By way of example, in cardiovascular tissue, the lack of an anisotropic network detrimentally alters the ventricular geometry, which leads to both systolic and diastolic dysfunction of the endogenous cardiovascular ECM and tissue structures.

One of the seminal MMPs activated during the inflammatory phase is macrophage elastase or MMP-12, which directly breaks down the ECM protein elastin and activates monocyte chemoattractant protein-1 (MCP-1). MCP-1 recruits monocytes (macrophage and dendritic cell progenitors), NK cells, T-lymphocytes, and dendritic cells to the sites of inflammation. Further, the recruited M1 type macrophages secrete additional MMP-12, thus creating a positive feedback loop that perpetuates the inflammatory phase and breakdown of endogenous ECM.

As evidenced by the graphical illustrations shown in FIGS. 16-19, when a statin augmented composition is delivered to damaged biological tissue, the statin augmented composition inhibits expression of MCP-1, which closes the positive feedback loop that perpetuates the detrimental breakdown of endogenous ECM. The noted inhibition of MCP-1 expression subsequently abates the migration of pro-inflammatory cells, including, monocytes, M1 type macrophages, memory T-cells, and dendritic cells, which produces an anti-inflammatory effect.

When the statin augmented composition comprises acellular ECM and cerivastatin and the noted statin, i.e. cerivastatin, augmented ECM composition is disposed proximate damaged biological tissue, the statin augmented ECM composition also inhibits expression of C-C chemokine receptor type 2 (CCR2), which is the receptor protein for MCP-1. The noted restriction of both MCP-1 and CCR2 expression provides an enhanced level of inflammation modulation of damaged biological tissue when a cerivastatin augmented ECM composition is disposed proximate thereto.

Thus, in some embodiments, the term "modulated healing" also refers to the ability of an ECM composition (and ECM/ECM-mimicking composition); particularly, a cerivastatin augmented ECM composition to modulate inflammation by, among other actions, restricting expression of MCP-1 and CCR2.

In some embodiments, "modulated healing" refers to the ability of an ECM composition (and/or ECM-mimicking composition and/or ECM/ECM-mimicking composition)

and, hence, cardiovascular prosthesis formed therefrom, of the invention to induce anti-microbial and anti-biofilm activity, which significantly enhance inflammation modulation of damaged biological tissue and, thereby, enhanced neovascularization, remodeling of the damaged biological tissue and regeneration of new tissue and tissue structures.

As also indicated above, in some embodiments, the ECM composition (and/or ECM-mimicking composition and/or ECM/ECM-mimicking composition) and, hence, cardiovascular prosthesis formed therefrom further comprises an antibiotic. ECM, ECM-mimicking and ECM/ECM-mimicking compositions comprising an antibiotic and hereinafter referred to as antibiotic augmented compositions.

According to the invention, when an antibiotic augmented composition and, hence, cardiovascular prosthesis formed therefrom is delivered directly, i.e. local delivery, to damaged biological tissue, the antibiotic augmented composition induces several significant biological processes, including anti-microbial and anti-biofilm activity, which, as indicated above, significantly enhance modulated healing, including inflammation modulation of the damaged biological tissue.

When an ECM composition (and/or an ECM/ECM-mimicking composition) comprising acellular ECM and, hence, cardiovascular prosthesis formed therefrom is disposed proximate damaged biological tissue, migrating endogenous cells bind to the damaged biological tissue, whereby a plurality of acellular ECM components are degraded or "broken-down" by the endogenous cells to form ECM products. The ECM products provide the "building-blocks" for regeneration of new tissue and tissue structures.

A significant portion of the ECM products comprise a particular subtype of peptides known as anti-microbial peptides (AMPs), which are a seminal component of acellular ECM.

AMPs are a subtype of anti-microbial (and anti-biofilm) peptide molecules, which provide a first line of defense against a plurality of pathogens; particularly, microbes, e.g., bacteria.

AMPs comprise a net positive charge, which provides AMPs with the ability to target and destroy microbes, such as bacteria, by disrupting the cell membranes and/or walls of the microbes.

When the antibiotic augmented composition comprising acellular ECM, i.e. an antibiotic augmented ECM composition, is disposed proximate (i.e. delivered to) damaged biological tissue, the antibiotic augmented ECM composition releases the antibiotic and AMPs into the damaged biological tissue. As indicated above, the released AMPs disrupt the cell membranes and/or walls of microbes, while the antibiotic disrupts the microbes' capacity to synthesize and, hence, repair the cell membrane and/or wall. The protective cell membrane and/or wall of the microbes is thus permanently destroyed and the microbes are rendered ineffective.

According to the invention, another seminal biochemical action or activity induced by an antibiotic augmented ECM composition and, hence, cardiovascular prosthesis formed therewith is anti-biofilm activity.

Biofilm comprises a colony of bacteria that are embedded within a self-produced matrix of extracellular polymeric substance (EPS), which comprises a conglomeration consisting generally of extracellular DNA (eDNA), proteins, and polysaccharides.

The primary seminal function of a biofilm is to protect the bacterial colonies from external assault; particularly, (i) anti-microbial agents, such as antibiotics and (ii) immune responses from a given host.

According to the invention, when an antibiotic augmented ECM composition and, hence, cardiovascular prosthesis of the invention is disposed proximate damaged biological tissue that contains a bacterial biofilm, the antibiotic augmented ECM composition and, hence, cardiovascular prosthesis releases matrix metalloproteinases (MMPs), which provide two seminal functions: (i) degrade a portion of the tissue during the remodeling and regeneration processes to form tissue products and (ii) degrade the EPS that forms the bacterial biofilm.

As also indicated above, when an antibiotic augmented ECM composition is disposed proximate damaged biological tissue, AMPs are released into the damaged biological tissue. The cationic properties of the AMPs provide AMPs with the ability to bind to DNA, which has an inherently anionic nature.

The AMPs are thus able to bind to the eDNA component of bacterial biofilms, which targets the eDNA for degradation by an endogenous immune response in the damaged biological tissue. The AMPs are also capable of disrupting the attachment of bacteria to the bacterial biofilm, which renders the bacteria planktonic and, thus, significantly easier to destroy in vivo via antibiotics and/or an in vivo immune response.

In some embodiments of the invention, the antibiotic augmented ECM composition preferably comprises vancomycin and gentamicin.

Vancomycin and gentamicin have distinct binding affinities for acellular ECM, which provides a "two-phase" antibiotic delivery profile: (i) a "bolus" antibiotic delivery profile and (ii) a sustained release antibiotic profile.

Vancomycin has a higher binding affinity for acellular ECM than gentamicin. Thus, according to the invention, when an antibiotic augmented ECM composition comprises vancomycin and gentamicin is disposed proximate to damaged biological tissue, by virtue of vancomycin's higher binding affinity for the acellular ECM, vancomycin is delivered to the damaged biological tissue at a substantially slower rate than the gentamicin, i.e. a sustained release delivery profile. Since gentamicin's binding affinity for acellular ECM is substantially lower than vancomycin's binding affinity, a bolus delivery of gentamicin to the damaged biological tissue is effectuated.

The initial bolus of gentamicin renders the microbes, e.g., bacteria, and biofilm at the damaged biological tissue site ineffective, while the sustained delivery of vancomycin prevents the colonialization of planktonic microbes and the subsequent formation of biofilms.

In some embodiments of the invention, the wt. % of the antibiotic in the ECM composition (and ECM-mimicking, ECM/ECM-mimicking, and statin augmented compositions of the invention) is in the range of approximately 0.0001-20 wt. %, more preferably, in the range of approximately 0.001-1 wt. %.

In some embodiments of the invention, the wt. % of the antibiotic in the ECM composition (and ECM-mimicking, ECM/ECM-mimicking, and statin augmented compositions of the invention) is less than approximately 0.0001 wt. %.

In a preferred embodiment, the wt. % of the antibiotic in the ECM composition (and ECM-mimicking, ECM/ECM-mimicking, and statin augmented compositions of the invention) is sufficient to induce several significant biological processes, including anti-microbial and anti-biofilm activity in vivo, e.g., disrupting the cell membranes and/or walls of microbes, without inducing an adverse biological response.

As also indicated above, in some embodiments of the invention, the ECM composition (and/or ECM-mimicking composition and/or ECM/ECM-mimicking composition) and, hence, cardiovascular prosthesis formed therefrom further comprises at least one additional biologically active agent or composition, i.e. an agent that induces or modulates a physiological or biological process, or cellular activity, e.g., induces proliferation, and/or growth and/or regeneration of tissue.

ECM, ECM-mimicking and ECM/ECM-mimicking compositions comprising a growth factor are hereinafter referred to as growth factor augmented compositions.

In some embodiments of the invention, the biologically active agent comprises a growth factor selected from the group comprising transforming growth factor-alpha (TGF-α), transforming growth factor-beta (TGF-β), basic fibroblast growth factor (bFGF), and vascular endothelial growth factor (VEGF).

According to the invention, when a growth factor augmented composition and, hence, cardiovascular prosthesis formed therefrom is disposed proximate damaged tissue, the growth factors link to and interact with at least one molecule in the composition and further induce and/or control modulated healing, i.e. inflammation modulation and/or host cell and/or tissue proliferation, and/or remodeling of damaged biological tissue, and regeneration of new tissue and tissue structures.

According to the invention, when a growth factor augmented composition comprises VEGF and a second growth factor, comprising bFGF, TGF-α or TGF-β and the noted growth factor augmented composition is disposed proximate damaged biological tissue, synergistic activity by and between VEGF and the second growth factor is induced; the synergistic activity comprising induced angiogenesis by VEGF, which facilitates cell proliferation and enhances bioremodeling of the damaged biological tissue induced by the second growth factor, i.e. bFGF, TGF-α or TGF-β.

In some embodiments of the invention, the biologically active agent comprises an exosome. As indicated above, exosomes comprise a lipid bilayer structure that contains or encapsulates a biologically active agent, such as a growth factor, e.g., TGF-β, TGF-α, VEGF and insulin-like growth factor (IGF-I), cytokine, e.g., interleukin-8 (IL-8), transcription factor and micro RNA (miRNA).

ECM, ECM-mimicking and ECM/ECM-mimicking compositions comprising an exosome are hereinafter referred to as exosome augmented compositions.

Exosomes significantly enhance the delivery of biologically active agents to cells through two seminal properties/capabilities. The first property comprises the capacity of exosomes to shield the encapsulated biologically active agents (via the exosome lipid bilayer) from proteolytic agents, which can, and often will, degrade unshielded (or free) bioactive molecules and render the molecules non-functional in biological tissue environments.

The second property of exosomes comprises the capacity to directly and, hence, more efficiently deliver biologically active agents to endogenous cells in the biological tissue. As is well known in the art, endogenous cells typically do not comprise the capacity to "directly" interact with "free" biologically active agents, such as growth factors. There must be additional biological processes initiated by the endogenous cells to interact directly with biologically active agents, e.g., expression of receptor proteins for or corresponding to the biologically active agents.

Exosomes facilitate direct interaction by and between endogenous cells and exosome encapsulated biologically active agents (and, hence, direct delivery of bioactive molecules to endogenous cells), which enhances the bioactivity of the agents.

According to the invention, when an exosome composition comprises acellular ECM and the exosome augmented composition is delivered to the damaged biological tissue, the noted exosome augmented ECM composition "concomitantly" induces a multitude of significant biological processes in vivo, including (i) significantly enhanced inflammation modulation of the damaged biological tissue, (ii) induced neovascularization, (iii) induced stem cell proliferation, (iv) induced remodeling of the damaged biological tissue, and (v) induced regeneration of new tissue and tissue structures with site-specific structural and functional properties, compared to acellular ECM alone.

By way of example, when an exosome augmented ECM composition comprising encapsulated IL-8 (and, hence, cardiovascular prosthesis formed therefrom) is disposed proximate damaged biological tissue, the exosome encapsulated IL-8 and, hence, tissue prosthesis modulates the transition of M1 type "acute inflammatory" macrophages to M2 type "wound healing" macrophages initiated by the acellular ECM.

By way of further example, when an exosome augmented ECM composition comprising encapsulated miRNAs (and, hence, cardiovascular prosthesis formed therefrom) is disposed proximate damaged biological tissue, the cardiovascular prosthesis induce enhanced stem cell proliferation via the delivery of exosome encapsulated miRNAs and transcription factors to the damaged biological tissue, which signals the endogenous stem cells to bind and/or attach to the acellular ECM and proliferate.

In some embodiments, the exosomes are derived and, hence, processed from an aforementioned tissue source. In some embodiments, the exosomes are processed and derived from a mammalian fluid composition including, but not limited to blood, amniotic fluid, lymphatic fluid, interstitial fluid, pleural fluid, peritoneal fluid, pericardial fluid and cerebrospinal fluid.

In some embodiments, exosomes are derived and, hence, processed from in vitro or in vivo cultured cells. According to the invention, exosomes can be derived from any one of the aforementioned cells, such as mesenchymal stem cells and hematopoietic stem cells.

In some embodiments, mesenchymal stem cells are cultured in a cell culture media under hypoxic conditions to induce a higher production rate of exosomes.

In some embodiments, mesenchymal stem cells are cultured on an aforementioned acellular ECM, where the mesenchymal stem cells condition the acellular ECM by releasing exosomes, which bind to the ECM composition to form an exosome augmented ECM composition and/or ECM/ECM-mimicking composition.

In some embodiments, the exosomes comprise semi-synthetically generated exosomes. According to the invention, the semi-synthetically generated exosomes can be derived from an exosome producing cell line.

By way of example, semi-synthetically generated exosomes can be generated by incubating mesenchymal stem cells in a medium comprising a predetermined concentration of any one of the aforementioned biologically active agents and/or pharmacological active agents and, after a predetermined period of time, removing the mesenchymal stem cells from the incubating medium and in vitro culturing using conventional cell culture techniques. The cell culture media employed can then be processed to isolate one or more exosome-encapsulated biologically active agents and/or pharmacological active agents.

According to the invention, the exosome-encapsulated biologically active agents and/or pharmacological active agents can be isolated from the cell culture media using any known conventional method, such as ultra-centrifugation.

According to the invention, the semi-synthetically generated exosomes markedly improve the efficacy of the aforementioned biologically active agents and/or the pharmacological active agents by providing a means of traversing the cell membrane of endogenous cells.

As indicated above, in some embodiments, the wt. % of the biologically active agent in the ECM composition (and ECM-mimicking, ECM/ECM-mimicking, and statin augmented compositions of the invention, discussed in detail below) is in the range of approximately 0.0001-20 wt. %, more preferably, in the range of approximately 0.001-1 wt.

In some embodiments, the wt. % of a biologically active and/or pharmacological agent in an ECM, ECM-mimicking and/or ECM/ECM-mimicking composition is preferably less than 0.001%, less than 0.01%, less than 0.1%, less than 0.5%, less than 1%, less than 2%, less than 5%, and less than 10%.

In some embodiments, the wt. % of a biologically active and/or pharmacological agent in an ECM, ECM-mimicking and/or ECM/ECM-mimicking composition is preferably greater than 0.0001%, greater than 0.001%, greater than 0.01%, greater than 0.1%, greater than 0.5%, greater than 1%, greater than 1.5%, greater than 2%, greater than 4%, greater than 5%, greater than 10%, greater than 12%, greater than 15%, and greater than 20%.

In a preferred embodiment, the wt. % of the biologically active agent in the ECM composition (and ECM-mimicking, ECM/ECM-mimicking, and statin augmented compositions of the invention) is sufficient to induce or modulate a physiological or biological process, without inducing an adverse biological response, e.g., a physiological response that is sufficient to induce a biological process and/or restrict a phase associated with biological tissue healing in vivo.

According to the invention, any of the compositions and, hence, cardiovascular prostheses referenced herein, such as an ECM composition, are configured to provide a single-stage agent delivery profile, i.e. comprise a single-stage delivery vehicle, wherein a modulated dosage of a biologically active and/or pharmacological agent is provided. In some embodiments, the compositions provide a multi-stage agent delivery profile, i.e. comprise a multi-stage agent delivery vehicle, wherein a plurality of biologically active and/or pharmacological agents are administered via a modulated dosage. Suitable single-stage and multi-stage agent delivery vehicles are disclosed in Co-Pending U.S. application Ser. Nos. 14/554,730, 14/957,995, 14/958,061 and 14/958,034, which are incorporated by reference herein.

In some embodiments, the cardiovascular prosthesis comprises an ECM-mimicking composition comprising PGS.

In some embodiments, the ECM-mimicking composition further comprises at least one of the aforementioned biologically active agents and/or pharmacological agents.

In some embodiments, the cardiovascular prostheses comprise an ECM/ECM-mimicking composition comprising acellular ECM and PGS.

In some embodiments, the ECM/ECM-mimicking composition further comprises at least one of the aforementioned biologically active agents and/or pharmacological agents.

As discussed in detail below, PGS provides numerous beneficial structural and biochemical actions or activities.

PGS Physical Properties

PGS is a condensate of the non-immunogenic compositions glycerol (a simple sugar alcohol) and sebacic acid (a naturally occurring dicarboxylic acid), wherein, glycerol and sebacic acid are readily metabolized when disposed proximate mammalian tissue. The non-immunogenic properties substantially limit the acute inflammatory responses typically associated with other "biocompatible" polymers, such as ePTFE (polytetrafluoroethylene), that are detrimental to bioremodeling and tissue regeneration.

As set forth in Co-pending U.S. application Ser. No. 14/566,359, which is incorporated by reference herein, the tensile strength of the PGS is at least 0.28±0.004 MPa. The Young's modulus and elongation of PGS are at least 0.122±0.0003 and at least 237.8±0.64%, respectively.

Thus, according to the invention, when a cardiovascular prosthesis of the invention comprises PGS, i.e. formed from a composition comprising PGS or includes a PGS layer or coating, the PGS enhances the mechanical strength of the prosthesis.

PGS Adhesive Properties

PGS also exhibits unique adhesive properties.

Thus, according to the invention, when a cardiovascular prosthesis comprises a PGS layer and/or PGS coated surface that is in contact with biological tissue, such as tissue of a cardiovascular structure, the prosthesis adheres thereto, which facilitates modulated healing by the prosthesis.

When a cardiovascular prosthesis comprises a PGS layer and/or PGS coated surface that is in contact with a non-coated or PGS coated surface of a second prosthesis structure, e.g., a second sheet member of a laminate structure, the PGS layer and/or PGS coated surface also adheres to the non-coated or PGS coated surface of the second prosthesis structure, e.g., second sheet member, which substantially reduces or eliminates dilation and/or delamination of the prosthesis structure or members.

ECM-Mimicking Properties/Actions

PGS also induces tissue remodeling and regeneration when administered to damaged tissue, thus, mimicking the seminal regenerative properties of acellular ECM and, hence, a composition formed therefrom. The mechanism underlying this behavior is deemed to be based on the mechanical and biodegradation kinetics of the PGS. Sant, et al., *Effect of Biodegradation and de novo Matrix Synthesis on the Mechanical Properties of VIC-seeded PGS-PCL scaffolds*, Acta. Biomater., vol. 9(4), pp. 5963-73 (2013) and Wang, et al., In Vivo *Degradation Characteristics of Poly (Glycerol Sebacate)*, J. Biomed. Mat. Res. Part (A), Vol. (66)1, pp. 192-197 (2003), incorporated by reference herein.

When an ECM and/or ECM/ECM-mimicking composition comprising acellular ECM and PGS is disposed proximate damaged tissue, such as damaged cardiovascular tissue, the synergistic action by and between PGS and acellular ECM provides an enhanced level of remodeling of the damaged tissue and regeneration of new tissue and tissue structures.

Degradation Modulation

PGS also modulates the degradation characteristics ECM and ECM/ECM-mimicking compositions and structures formed therefrom.

By way of example, when a cardiovascular prosthesis comprises a PGS layer or PGS coated outer surface and the cardiovascular prosthesis is disposed proximate damaged biological tissue, e.g., damaged cardiovascular tissue, the PGS layer or PGS coated outer surface modulates degradation of the prosthesis.

In some embodiments, the cardiovascular prosthesis exhibits a linear degradation profile, which induces an enhanced level of modulated healing, including remodeling of damaged biological tissue and regeneration of new tissue and tissue structures.

In some embodiments, the linear degradation profile provided by the PGS in an ECM or ECM/ECM-mimicking composition allows the cardiovascular prosthesis formed therefrom to degrade at a rate that reduces the probability of maladaptive remodeling, e.g., fibrosis. Thus, the unique spatial properties of the combined acellular ECM and PGS components of a cardiovascular prosthesis further enhance modulated healing of damaged tissue.

In some embodiments of the invention, the ECM-mimicking composition comprises PGS and poly($\varepsilon$-caprolactone) (PCL). According to the invention, the addition of PCL to the ECM-mimicking biomaterial composition enhances the structural integrity of the cardiovascular prostheses and further modulates the degradation of a cardiovascular prostheses formed therefrom.

In some embodiments, the ECM-mimicking composition comprises poly(glycerol sebacate) acrylate (PGSA), which, according to the invention, can be crosslinked, i.e. cured, via the combination of a photoinitiator and/or radiation.

According to the invention, suitable photoinitiators for radiation induced crosslinking comprise, without limitation, 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl, methylcyclopentadienyl manganese tricarbonyl and any organometallatic photoinitiator that produces free radicals or cations.

According to the invention, suitable radiation wavelengths for crosslinking and/or curing the ECM-mimicking composition comprise, without limitation, visible light; particularly, radiation in the range of approximately 380-750 nm, and ultraviolet (UV) light, particularly, radiation in the range of 10-400 nm, which includes extreme UV (10-121 nm), vacuum UV (10-200 nm), hydrogen lyman $\alpha$-UV (121-122 nn), Far UV (122-200 nn), Middle UV (200-300 nm), Near UV (300-400 nm), UV-C (100-280 nm), UV-B (280-315 nm) and UV-A (315-400 nm) species of UV light.

In some embodiments, the ECM-mimicking composition comprises a co-polymer of PGSA and polyethylene glycol (PEG) diacrylate.

In some embodiments, when a cardiovascular prosthesis is disposed proximate damaged biological tissue, modulated healing is effectuated through the structural features of the cardiovascular prosthesis. The structural features of the cardiovascular prosthesis provide the spatial and mechanical cues to modulate endogenous cell polarity and alignment. The structural features of the cardiovascular prosthesis further modulate endogenous cell proliferation, migration and differentiation.

As discussed in detail above, the cardiovascular prostheses of the invention can comprise various structures and compositions, including, but not limited to, particulate structures, mesh constructs, encasement structures, coated structures and multi-sheet laminate structures.

Exemplar cardiovascular prostheses of the invention will now be described in detail. It is, however, understood that the invention is not limited to the structures described below. Indeed, as indicated above, the cardiovascular prostheses of the invention can comprise various structures and compositions.

As also indicated above, the cardiovascular prostheses can be employed to treat various disorders, including, without limitation, atrial fibrillation (pre- and post-operative) and the root causes thereof, damaged or diseased biological tissue, e.g., infarct tissue, damaged and diseased mammalian organs and structures, e.g., infarct tissue, and damaged and diseased mammalian organs and structures, e.g., cardiac vessels and valves, myocardium, pericardium, arteries, trachea, etc.

Sheet Structures

In some embodiments of the invention, the cardiovascular prostheses comprise or are formed with sheet members.

Figure 2:
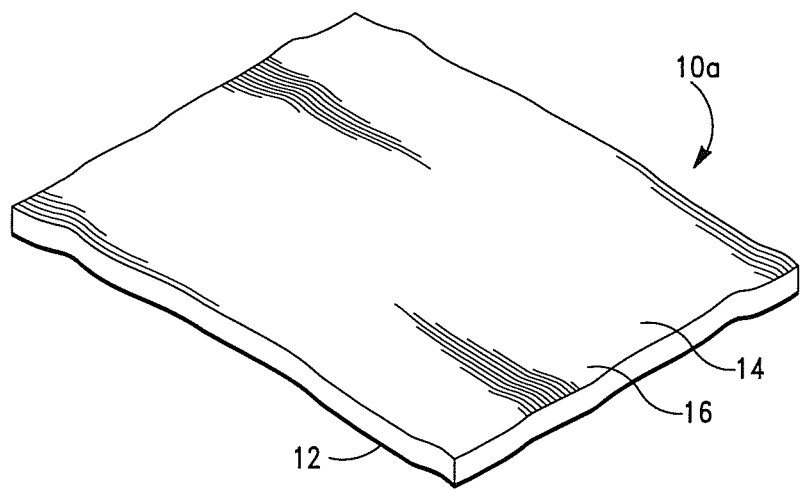
FIG. 2 is a perspective view of one embodiment of a prosthesis sheet member, in accordance with the invention.
Figure 3:
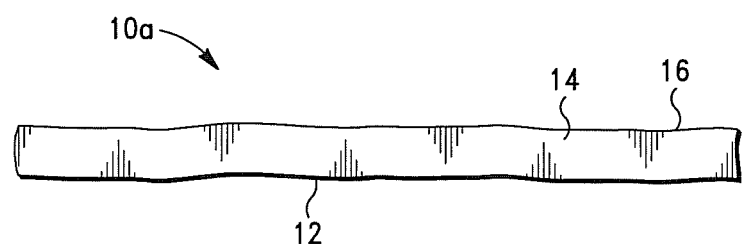
FIG. 3 is front plan view of the prosthesis sheet member shown in FIG. 2, in accordance with the invention.

Referring now to FIGS. 2 and 3, there is shown one embodiment of a sheet member of the invention. As illustrated in FIGS. 2 and 3, the sheet member 10a comprises a top surface 14 and a bottom surface 12. In some embodiments of the invention, the top surface 14 defines a tissue contacting surface.

In some embodiments, the sheet member 10a comprises one of the aforementioned ECM compositions.

In some embodiments, the sheet member 10a comprises one of the aforementioned ECM-mimicking compositions.

In some embodiments, the sheet member 10a comprises one of the aforementioned ECM/ECM-mimicking compositions.

As set forth in Co-Pending application Ser. No. 14/566,306, which is incorporated by referenced herein, in some embodiments, at least one surface 14, 12 of the sheet member 10a comprises a crosslinked surface. In the illustrated embodiment, the top surface 14 comprises a crosslinked surface 16.

In some embodiments of the invention, the crosslinked surface 16 comprises a chemically induced crosslinked surface.

In some embodiments of the invention, the crosslinked surface 16 comprises an energy induced crosslinked surface.

According to the invention, the crosslinked surface 16 of the sheet member 10a is configured to adhere to biological tissue and/or a second sheet member of a prosthesis structure, such as the laminate structure described below, whereby dilation and/or delamination of the structure is substantially reduced or eliminated.

Figure 4:
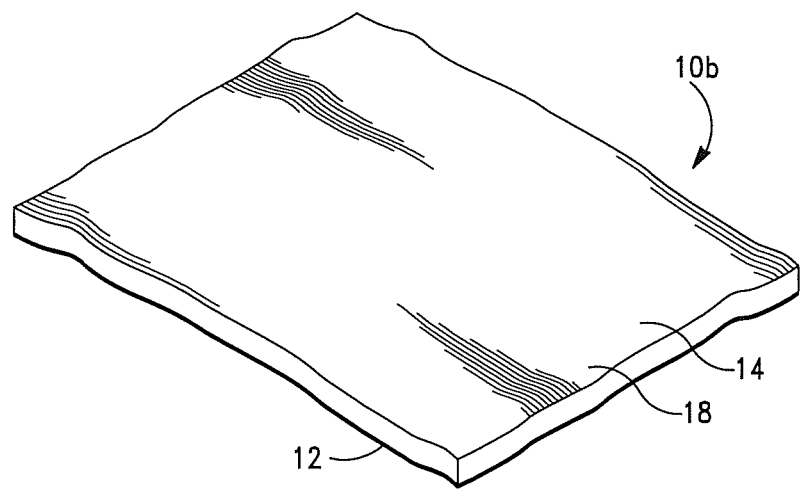
FIG. 4 is a perspective view of another embodiment of a prosthesis sheet member, in accordance with the invention.
Figure 5:
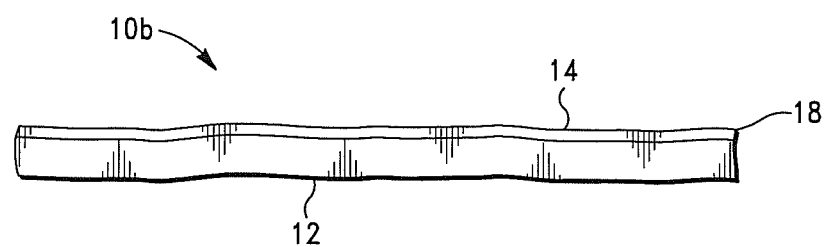
FIG. 5 is front plan view of the prosthesis sheet member shown in FIG. 4, in accordance with the invention.

Referring now to FIGS. 4 and 5, there is shown another embodiment of a sheet member of the invention. As illustrated in FIGS. 3 and 4, the sheet member 10b similarly comprises bottom and top surfaces 12, 14.

In the illustrated embodiment, at least one surface 12, 14 of the sheet member 10b comprises an outer coating. In some embodiments, as illustrated in FIG. 4, the top surface 14 of the sheet member 10b comprises a coated surface or layer 18. In some embodiments, the coated or layered top surface 14 similarly defines a tissue contacting surface.

In some embodiments, the coated surface or layer 18 comprises at least one of the aforementioned ECM compositions.

In some embodiments, the coated surface or layer 18 comprises at least one of the aforementioned ECM-mimicking compositions.

In some embodiments, coated surface or layer 18 comprises at least one of the aforementioned ECM/ECM-mimicking compositions.

In some embodiments of the invention, the sheet members 10a, 10b and/or coated surface or layer 18 further comprise at least one of the aforementioned biologically active agents or compositions.

In some embodiments of the invention, the ECM sheet members 10a, 10b and/or coated surface or layer 18 further comprise at least one of the aforementioned pharmacological agents or compositions.

According to the invention, the ECM sheet members 10a, 10b can be employed to construct various cardiovascular prosthesis structures, including, without limitation, single sheet structures, e.g., grafts, such as described in U.S. Pat. No. 8,877,224, and multi-sheet structures, such as described in Co-Pending application Ser. Nos. 14/566,359, 14/953,548 and 14/566,306. The noted applications are incorporated by reference herein in their entirety.

The single and multi-sheet structures can also comprise various shapes and dimensions to accommodate various applications.

Figure 6:
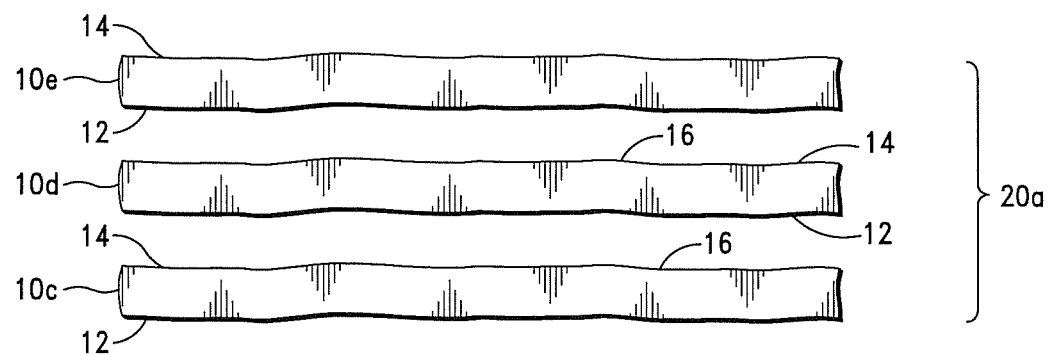
FIG. 6 is a front plan view of one embodiment of a multi-sheet prosthesis structure in a pre-lamination configuration, in accordance with the invention.
Figure 7:
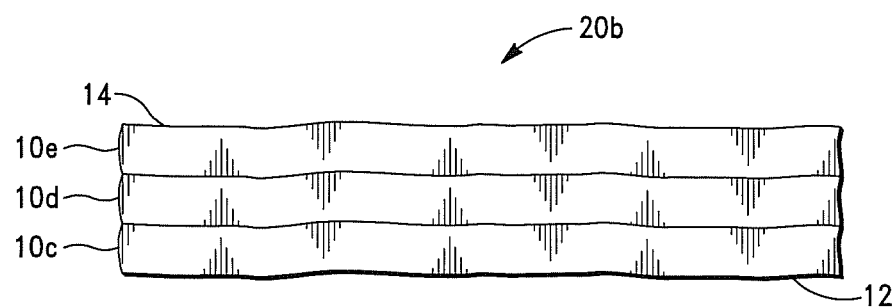
FIG. 7 is a front plan view of the multi-sheet prosthesis structure shown in FIG. 6 in a laminated configuration, in accordance with the invention.
Figure 8:
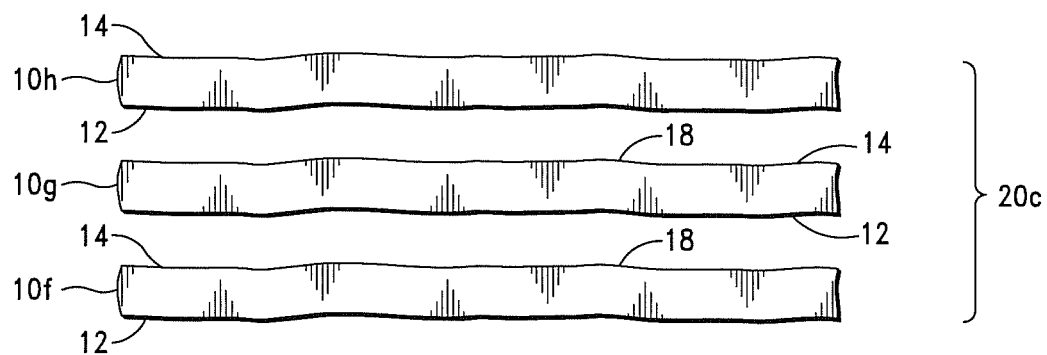
FIG. 8 is a perspective view of another embodiment of a multi-sheet prosthesis structure in a pre-laminated configuration, in accordance with the invention.

Referring now to FIGS. 6-9, there are shown two (2) embodiments of multi-sheet prosthesis structures of the invention. Referring to FIGS. 6 and 8, there is shown the multi-sheet prosthesis structures in a pre-lamination configuration (denoted 20a, 20c). As illustrated in FIGS. 6 and 8, the multi-sheet structures 20a and 20c comprise three (3) sheet members 10c, 10d, 10e and 10f, 10g, 10h, respectively.

According to the invention, the multi-sheet prosthesis structures can also comprise less or more than three (3) sheet members, e.g., two (2) sheet members, five (5) sheet members, etc.

As illustrated in FIG. 6, in some embodiments of the invention, the first and second sheet members 10c, 10d comprise a top crosslinked surface 16 that is configured to adhere to the bottom surface 12 of the adjoining sheet members 10d, 10e to form the laminate structure shown in FIG. 7 with a non-crosslinked top and bottom surface.

Figure 9:
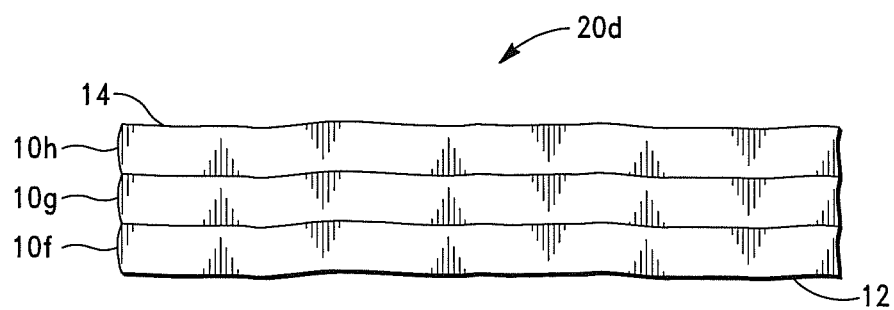
FIG. 9 is a front plan view of the multi-sheet prosthesis structure shown in FIG. 8 in a laminated configuration, in accordance with the invention.

As illustrated in FIG. 8, in some embodiments of the invention, the first and second sheet members 10f, 10g comprise a biomaterial coated surface 18 that is similarly configured to adhere to the bottom surface 12 of the adjoining sheet members 10g, 10h to form the laminate structure shown in FIG. 9.

In some embodiments of the invention, the biomaterial coated surface 18 comprises one of the aforementioned ECM-mimicking compositions.

In some embodiments of the invention, the biomaterial coated surface 18 comprises one of the aforementioned ECM/ECM-mimicking compositions.

As discussed in detail above, the biomaterial coated surface 18 is also configured to (i) adhere the multi-sheet structure 20d to biological tissue and (ii) modulate degradation of the multi-sheet structure 20d when the multi-sheet structure 20d is in contact with biological tissue.

According to the invention, the ECM sheet members 10a, 10b can be employed to form an encasement structure having a cavity therein that is configured to receive and, hence, encase a medical device and/or any one of the aforementioned ECM, ECM-mimicking or ECM/ECM-mimicking compositions and/or biologically active or pharmacological agents.

According to the invention, the encasement structures can comprise various shapes and sizes to accommodate virtually all shapes and sizes of medical devices and quantities of compositions.

Illustrative are the encasement structures described in U.S. Pat. Nos. 8,758,448, 9,066,993, 9,333,277 and 9,283,302 and Co-Pending U.S. application Ser. Nos. 14/818,757, 14/819,964, 14/571,639, 14/571,679, 14/685,755, 14/833,327, 14/833,340, 14/833,354, 14/833,373 and 14/833,404, which are incorporated by reference herein in their entirety.

Figure 10:
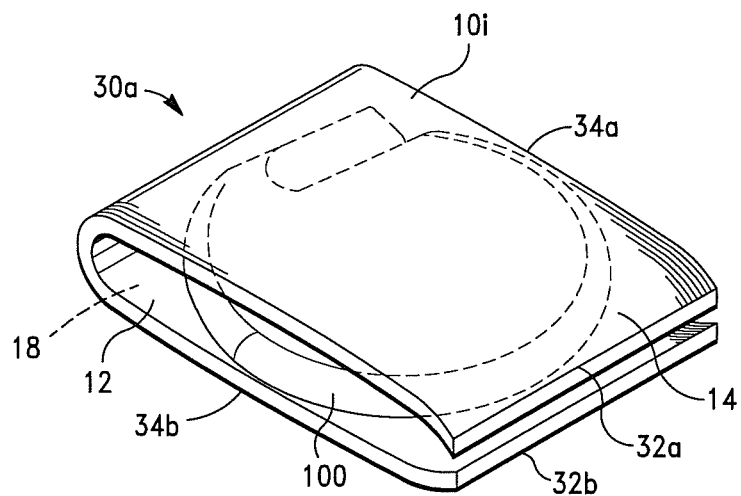
FIG. 10 is a perspective view one embodiment of a prosthesis encasement structure, in accordance with the invention.
Figure 11:
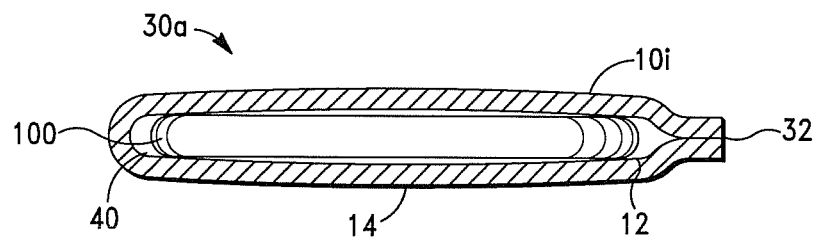
FIG. 11 is a front plan view of the prosthesis encasement structure shown in FIG. 10, in accordance with the invention.
Figure 12:
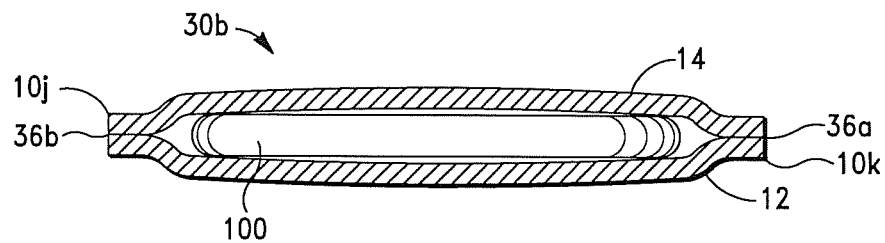
FIG. 12 is a perspective view of another embodiment of a prosthesis encasement structure, in accordance with the invention.

Referring now to FIGS. 10-12, two (2) embodiments of encasement structures will be described in detail.

Referring first to FIG. 10, there is shown an embodiment of an encasement structure 30a in a folded, pre-lamination configuration. As illustrated in FIG. 9, the encasement structure 30a preferably comprises one (1) sheet member 10i.

In some embodiments of the invention, sheet member 10i comprises sheet 10a shown in FIGS. 1 and 2 (denoted 10i). According to the invention, the sheet member 10i can also comprise sheet member 10b shown in FIGS. 4 and 5.

According to the invention, more than one (1) sheet member 10i can be employed to construct the encasement structure 30a (and 30b discussed below), wherein a multi-sheet encasement structure is provided.

As illustrated in FIGS. 10 and 11, the encasement structure 30a comprises atop surface 14, sides 34a, 34b, and edge regions 32a, 32b.

In some embodiments of the invention, at least one (1), preferably, both sides 34a, 34b are laminated to form a pouch structure having a cavity 40 therein that is preferably configured to encase a medical device 100 therein.

As indicated above, in some embodiments of the invention, sheet member 10i comprises sheet member 10b shown in FIGS. 4 and 5, comprising an ECM-mimicking or ECM/ECM-mimicking coated surface 18. In such embodiments, when the sheet member 10i is folded over the coated surface (wherein the coated surface 18 forms or defines the encasement structure cavity 40), the sides 34a, 34b adhere and seal the encasement structure about sides 34a, 34b.

Referring now to FIG. 12, there is shown another embodiment of an encasement structure 30b. As illustrated in FIG. 12, the encasement structure 30b preferably comprises two (2) ECM sheet members 10j, 10k that are joined on at least one end 36a, 36b. According to the invention, the end or ends 36a, 36b can similarly be joined by laminating the end or ends 36a, 36b or, as described above, employing at least one sheet member comprising an ECM-mimicking or ECM/ECM-mimicking coated surface Mesh Structures According to the invention, the cardiovascular prostheses can also comprise mesh constructs comprising at least one biodegradable fiber. In some embodiments, the cardiovascular prostheses comprise a plurality of biodegradable fibers, such as described in Co-Pending U.S. application Ser. Nos. 14/554,730, 14/957,995 and 14/958,034, which are incorporated by reference herein.

Figure 13:
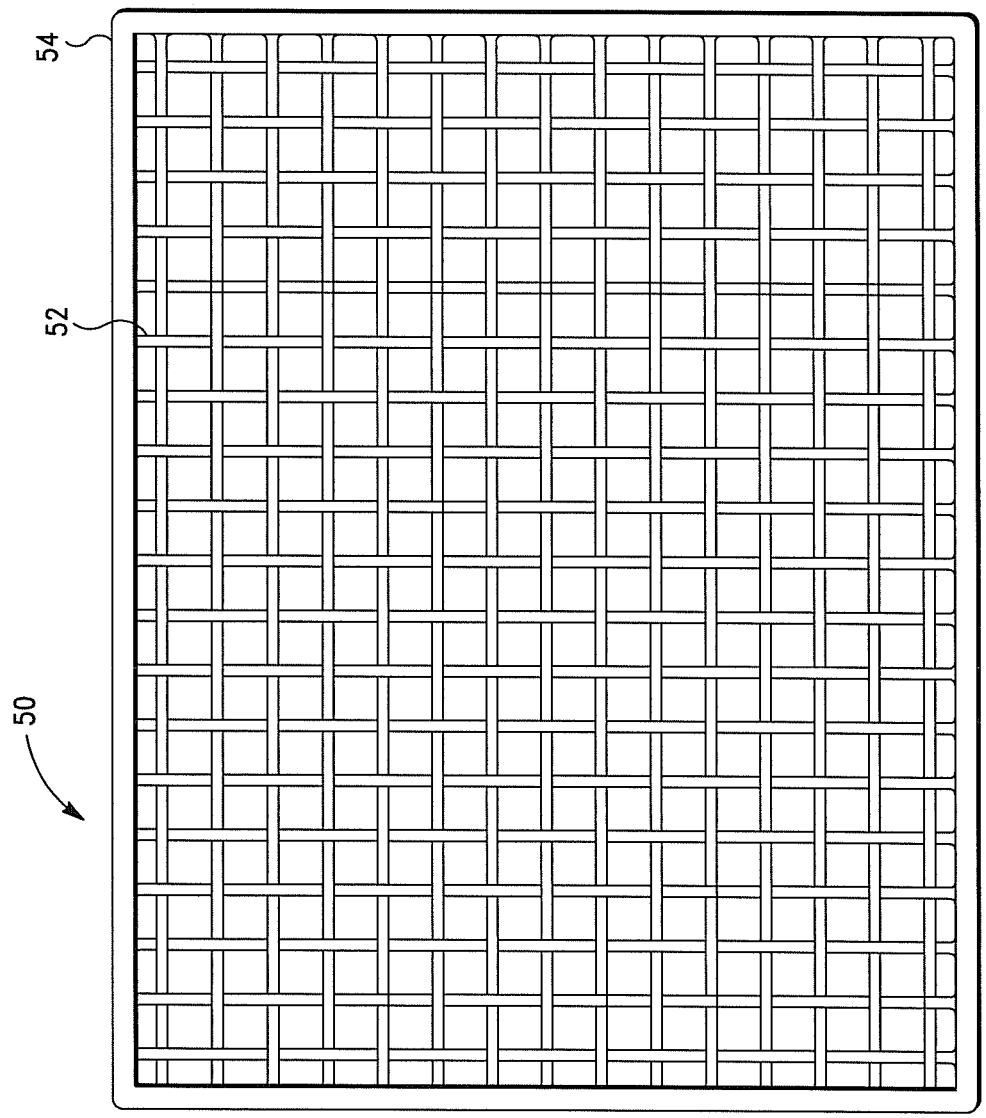
FIG. 13 is a perspective view of one embodiment of a prosthetic mesh structure, in accordance with the invention.

According to the invention, the biodegradable fibers can be arranged or oriented in various configurations, i.e. mesh patterns, to form a mesh fiber member or construct, such as shown in FIG. 13.

Referring now to FIG. 13, in some embodiments of the invention, the mesh constructs 50 comprise a plurality of substantially perpendicular interwoven or intersecting biodegradable fibers 52 contained by a restraining edge 54.

In some embodiments, the biodegradable fiber comprises at least one of the aforementioned ECM compositions.

In some embodiments, the biodegradable fiber comprises at least one of the aforementioned ECM-mimicking compositions.

In some embodiments, the biodegradable fiber comprises at least one of the aforementioned ECM/ECM-mimicking compositions.

In some embodiments, the biodegradable fiber comprises at least one of the aforementioned biologically active and/or pharmacological agents.

According to the invention, the mesh constructs can comprise any combination of ECM, ECM-mimicking and/or ECM/ECM-mimicking composition fibers.

According to the invention, the mesh constructs can also comprise biodegradable fibers comprising different compositions and/or multi-composition fibers, e.g., coated fibers.

Particulate Structures

According to the invention, the cardiovascular prostheses can also comprise particulate structures, such as described in U.S. Pat. Nos. 9,072,816, 9,119,899, 8,962,324 and 8,568,761 and Co-Pending U.S. application Ser. No. 14/566,404, which are incorporated by reference herein in their entirety.

According to the invention, the particulate structures can comprise any of the aforementioned ECM, ECM-mimicking and/or ECM/ECM-mimicking compositions and/or a mixture thereof.

Figure 14:
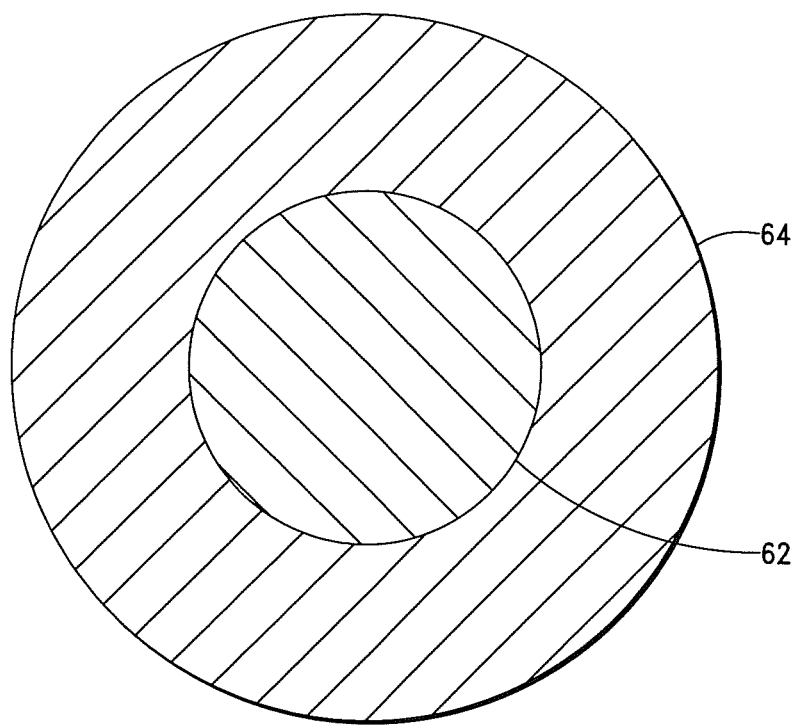
FIG. 14 is a front perspective view of one embodiment of a prosthetic particulate structure, in accordance with the invention.

Referring now to FIG. 14, in some embodiments of the invention, the particulate structures comprise a core 62 and outer layer (or coating) 64, such as described Co-Pending U.S. application Ser. Nos. 14/832,109 and 14/832,163, which are incorporated by reference herein in their entirety.

According to the invention, the core and/or outer layer 64 can similarly comprise any of the aforementioned ECM, ECM-mimicking and/or ECM/ECM-mimicking compositions and/or a mixture thereof.

In some embodiments of the invention, the outer layer comprises an ECM-mimicking and/or ECM/ECM-mimicking composition. According to the invention, when the particulate structure outer layer comprises an ECM-mimicking and/or ECM/ECM-mimicking composition, the outer layer (i) enhances the structural integrity of the particulate structure and (ii) modulates the degradation characteristics of the particulate structure when disposed proximate biological tissue.

As described in Co-Pending U.S. application Ser. No. 14/832,109, various conventional means can be employed to form a particulate structure of the invention.

In some embodiments of the invention, the cardiovascular prostheses comprise a plurality of the particulate structures. According to the invention, the particulate structures can be in the form of mixed liquids, mixed emulsions, mixed gels, mixed pastes, or mixed solid particulates. The liquid or semi-solid components of the particulate compositions can also comprise various concentrations.

EXAMPLES

The following examples are provided to enable those skilled in the art to more clearly understand and practice the present invention. They should not be considered as limiting the scope of the invention, but merely as being illustrated as representative thereof.

Example 1

Assessment of the Physiological Effects of a Cerivastatin Augmented Sheet Member A study was performed using a canine model in order to evaluate the physiological effects of various concentrations of cerivastatin in a sheet member comprising acellular ECM derived from small intestine submucosa (SIS), i.e. CorMatrix® acellular ECM patches, at 2 and 24 hrs post-implantation in canine myocardium.

The study included a total of four (4) treatment groups consisting of two (2) canines per treatment group. The four treatment groups consisted of a control group where two (2) canines were treated with an ECM sheet member derived from SIS without cerivastatin. The remaining three (3) treatment groups comprised groups of two (2) canines treated with cerivastatin augmented sheet members having 0.1 mg, 0.3 mg and 1 mg of cerivastatin per ECM sheet member.

The cerivastatin was impregnated into a 9 cm×9 cm sheet member by incubating the sheet member in a solution of phosphate buffered saline (PBS) and cerivastatin for 24 hours.

After the sheet members were prepared and impregnated with cerivastatin, eight (8) canines were prepared for surgery. The canines received anesthetic premedication, including 1 mg of Atropine and 0.15 mg of burenorphine, followed by anesthetic induction with propofol 100-300 mg or Pentothal 250-500 mg via intravenous injection. After the canines were anesthetized, a baseline blood sample and a pericardium fluid sample were collected from all eight (8) of the canine subjects.

A sternotomy was performed on all eight (8) of the canine subjects. The pericardial sac was isolated and a section of the pericardium was excised. A cerivastatin augmented sheet member was sutured to the excised region of the pericardium of six (6) of the canines as a closure device. The sheet members without cerivastatin were sutured to the excised region of the pericardium as a closure device for the remaining two (2) canines.

After 2 hours, a blood serum sample was collected from four (4) of the canines. After 24 hours, a blood serum sample was collected from the remaining four (4) canines. Cardiac tissue samples were subsequently harvested from the hearts of the canines, cut in half, placed in cryotubes, and flash frozen in liquid nitrogen. Samples were stored in a −80° C. freezer until used.

The tissue gene expression of MCP-1 and CCR2 were determined using reverse transcription polymerase chain reaction (RT-PCR).

Figure 15:
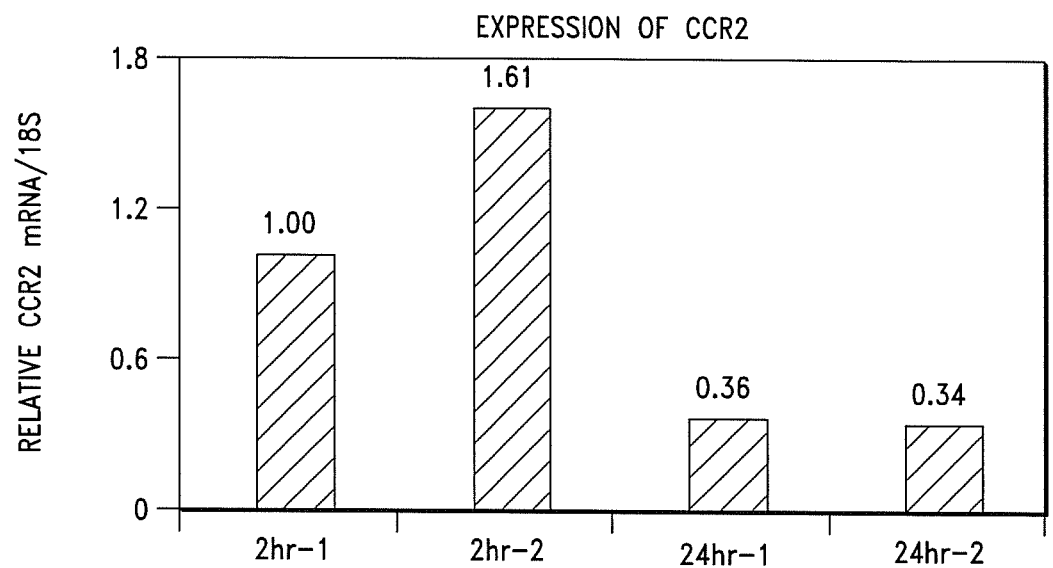
FIG. 15 is a graphical illustration of in vivo C-C chemokine receptor type 2 (CCR2) expression as a function of time for a cerivastatin augmented ECM prosthesis, in accordance with the invention.
Figure 16:
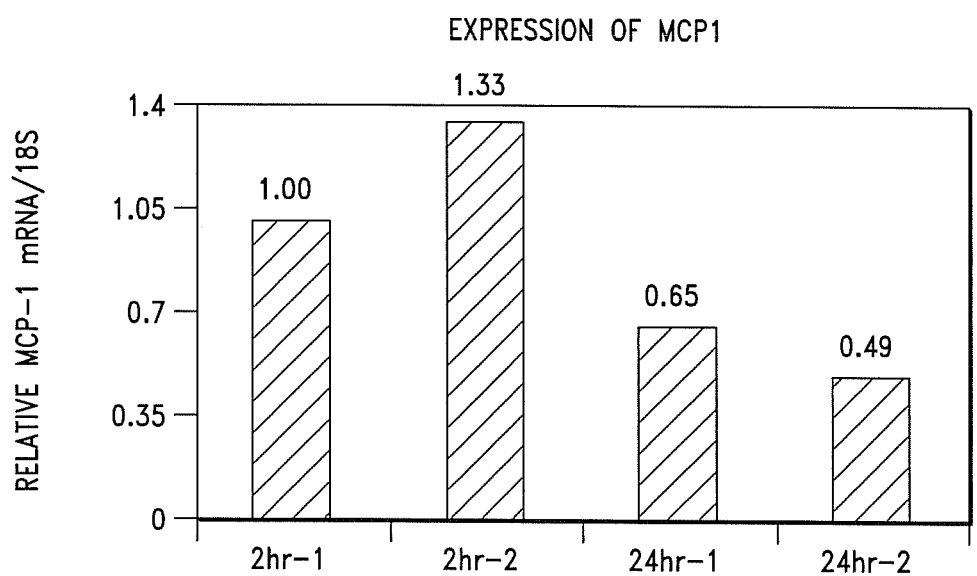
FIG. 16 is a graphical illustration of in vivo monocyte chemoattractant protein-1 (MCP-1) expression as a function of time for a cerivastatin augmented ECM prosthesis, in accordance with the invention.

FIGS. 15 and 16 show CCR2 and MCP-1 mRNA/18 s concentrations for the cardiac tissue samples harvested at the 2 hr. time point, compared to the CCR2 and MCP-1 mRNA/18 s concentrations for the tissue samples harvested at the 24 hour time point, respectively.

As reflected in FIGS. 15 and 16, when a cerivastatin augmented sheet member of the invention (and, hence, prosthesis structure formed therewith), is disposed proximate to damaged cardiovascular tissue, the cerivastatin augmented sheet member restricts expression of MCP-1 and CCR2 and, thereby, modulates inflammation of the damaged cardiovascular tissue.

Example 2

Anti-Inflammatory Activity of Cerivastatin Delivered with an Cerivastatin Augmented Sheet Member In the following study, the activity of cerivastatin release from a cerivastatin augmented sheet member comprising acellular ECM derived from SIS was assessed using an in vitro transwell assay. Human monocytic cells, i.e. THP-1 cells, were seeded by preparing a solution of THP-1 cells at $6\times10^5$ cells/ml and loading the solution of THP-1 cells into the bottom of 12-well transwell plates.

The transwell assay included four (4) treatment groups, including a control group consisting of untreated THP-1 cells, a first control group consisting of THP-1 cells treated with 200 ng/ml lipopolysaccharide (LPS) alone, a second control group consisting of THP-1 cells treated with 200 ng/ml LPS and an ECM sheet member comprising SIS derived from SIS, and a treatment group consisting of THP-1 cells treated with 200 ng/ml LPS and a cerivastatin augmented ECM sheet member.

The THP-1 cells were treated with 200 ng/ml LPS to stimulate the production of MCP-1.

Over the course of four (4) days, seeded THP-1 cells were harvested on each of the four (4) days of the study. Each of the harvested cell samples were collected in a sealable vial and centrifuged to separate the liquid media from the THP-1 cells. The liquid media, i.e. supernatant, was collected for use in an enzyme-linked immunosorbent assay. The THP-1 cells were also collected and used for RNA extraction and quantitative PCR.

Figure 17:
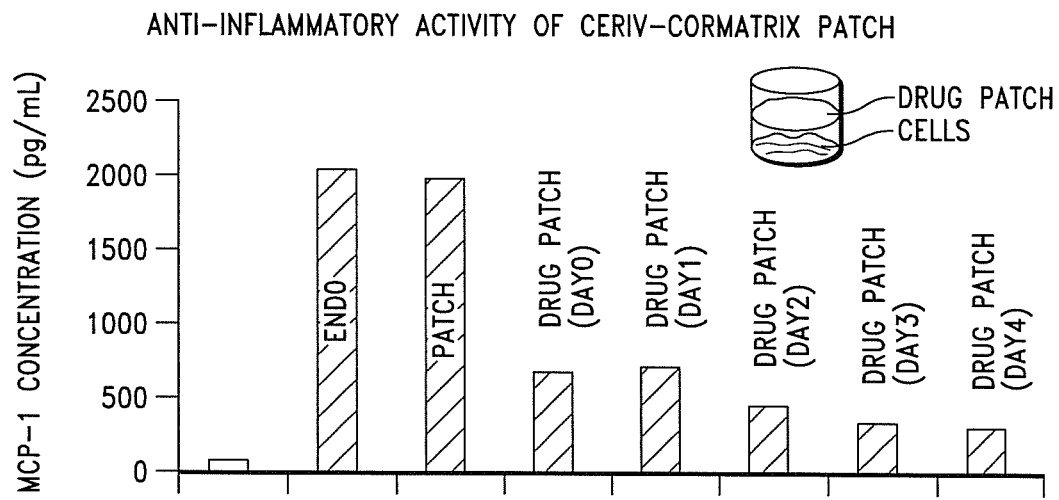
FIG. 17 is a graphical illustration of lipopolysaccharide (LPS) induced expression of MCP-1 in a human monocytic cell line; particularly, THP-1 cells, as a function of time for a non-cerivastatin augmented ECM prosthesis, in accordance with the invention.
Figure 18:
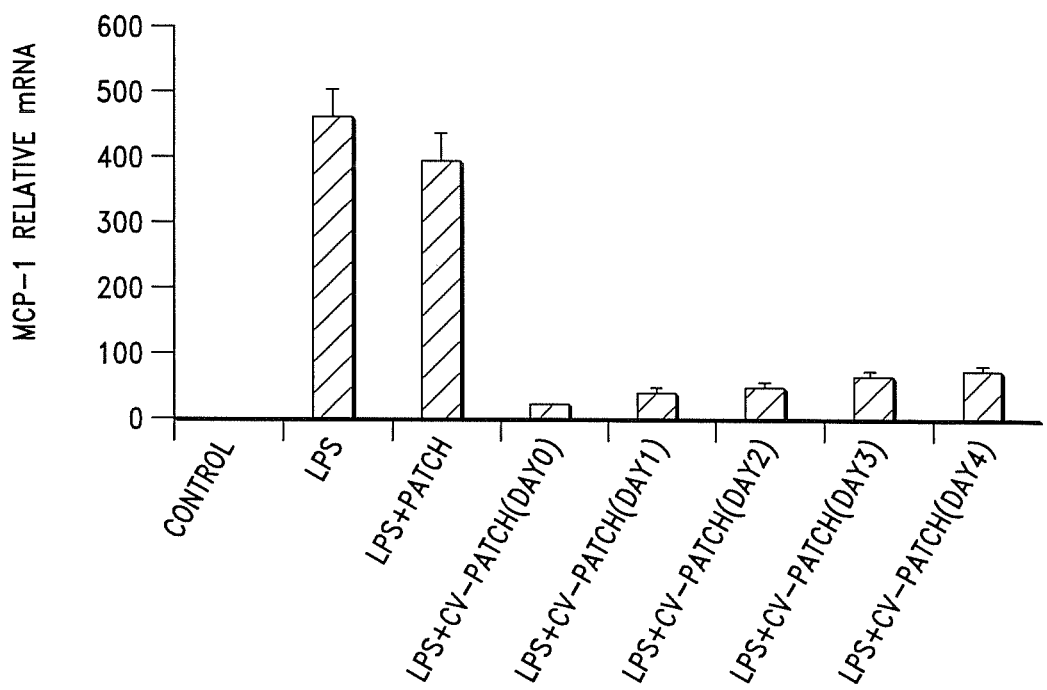
FIG. 18 is a graphical illustration of LPS induced expression of MCP-1 in THP-1 cells as a function of time for a cerivastatin augmented ECM prosthesis, in accordance with the invention.

FIGS. 17 and 18 reflect that treatment with 200 ng/ml of LPS induced expression of MCP-1 in THP-1 cells, and the placement of the sheet member without cerivastatin on the seeded THP-1 cells did not produce a significant change in MCP-1 expression. Conversely, the placement of the cerivastatin augmented sheet member on the seeded THP-1 cells restricted MCP-1 expression. The restriction of MCP-1 was maintained over the entire course of the four (4) day experiment.

The results from the transwell assay further confirm that a cerivastatin augmented sheet member (and, hence, cardiovascular prosthesis formed therewith) is capable of modulating inflammation by restricting MCP-1 expression.

Example 3

Determination of In Vitro Anti-Inflammatory Activity of Cerivastatin Released from a Cerivastatin Augmented Sheet Member In the following study the activity of cerivastatin release from a cerivastatin augmented sheet member comprising acellular ECM derived from SIS was similarly assessed using the human monocytic cell line THP-1.

The THP-1 cells were seeded by preparing a solution of THP-1 cells at $6\times10^5$ cells/ml and loading the solution of THP-1 cells onto a cell culture plate.

The in vitro assay included six (6) treatment groups, including a first control group consisting of untreated THP-1 cells, a second control group consisting of THP-1 cells treated with 200 ng/ml lipopolysaccharide (LPS) alone, further treatment groups consisting of THP-1 cells treated with 200 ng/ml LPS and 0.1 µM of cerivastatin, 200 ng/ml LPS and 0.5 µM of cerivastatin, 200 ng/ml LPS and 1 M of cerivastatin and 200 ng/ml LPS and 5 µM of cerivastatin.

The THP-1 cells were similarly treated with 200 ng/ml LPS to stimulate the production of MCP-1.

Each of the cell samples were harvested and collected in a sealable vial and centrifuged to separate the liquid media from the THP-1 cells. The THP-1 cells were collected and used for RNA extraction and quantitative PCR.

Figure 19:
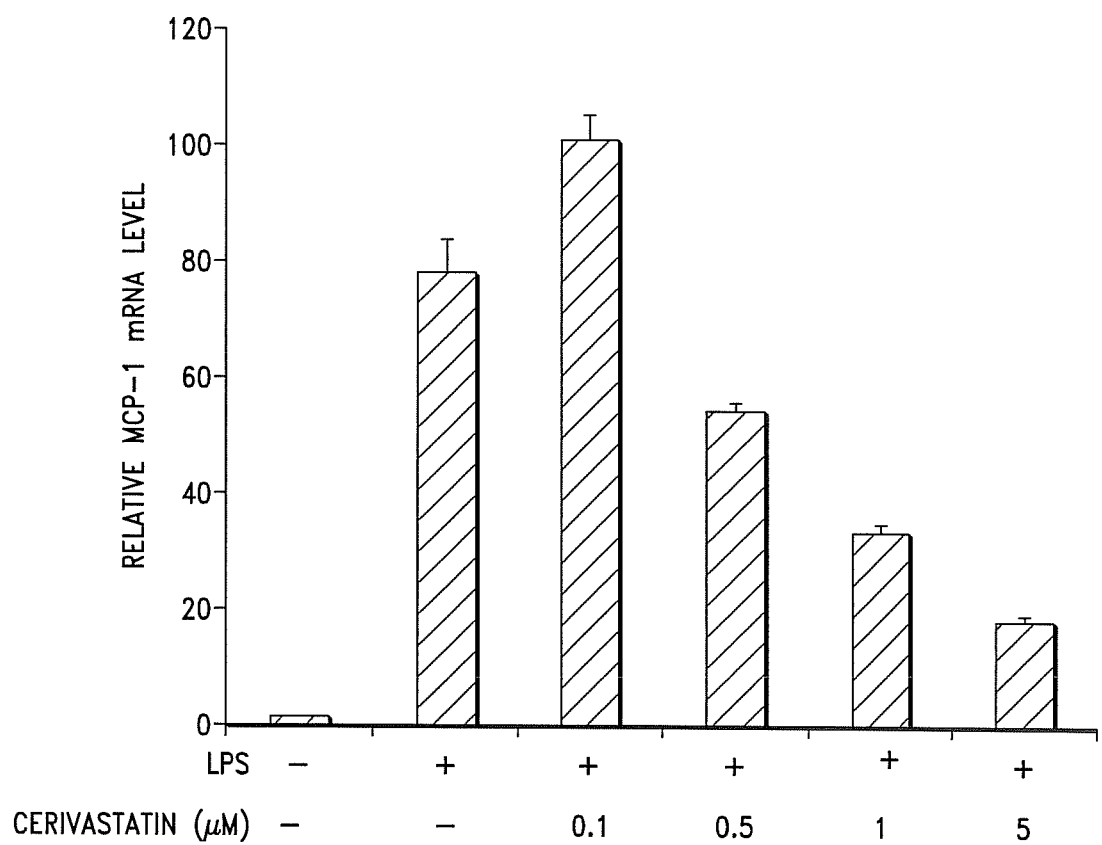
FIG. 19 is a graphical illustration of LPS induced expression of MCP-1 in THP-1 cells as a function of time for cerivastatin augmented ECM prostheses having various concentrations of cerivastatin, in accordance with the invention.

As reflected in FIG. 19, the expression of MCP-1 mRNA was inhibited by cerivastatin in a concentration-dependent manner, i.e. higher concentrations of cerivastatin resulted in greater restriction of MCP-1 expression.

Example 4

Determination of MCP-1 and CCR2 Restriction by Cerivastatin Compared to Other Statins In the following study, the activity of cerivastatin and other statins, including simvastatin, lovastatin and atorvastatin, was similarly assessed using the human monocytic cell line THP-1.

The THP-1 cells were similarly seeded by preparing a solution of THP-1 cells at $6\times10^5$ cells/ml and loading the solution of THP-1 cells onto a cell culture plate.

The in vitro assay included six (6) treatment groups, including one (1) control group consisting of untreated THP-1 cells, one (1) positive control group consisting of THP-1 cells treated with tumor necrosis factor alpha (TNF-α) alone, four (4) treatment groups consisting of THP-1 cells treated with TNF-α and cerivastatin, TNF-α and simvastatin, TNF-α and lovastatin and TNF-α and atorvastatin.

In this study, the THP-1 cells were treated with TNF-α to stimulate the production of CCR2.

Each of the six (6) THP-1 cell samples were harvested and collected in a sealable vial and centrifuged to separate the liquid media from the THP-1 cells. The THP-1 cells were then collected and used for RNA extraction and quantitative PCR.

It was found that cerivastatin was capable of substantially restricting expression of CCR2. Simvastatin, lovastatin and atorvastatin did not, however, restrict CCR2 expression at levels comparable to cerivastatin.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A cardiovascular prosthesis, consisting of:
   an Extracellular Matrix (ECM)-mimicking composition consisting of a plurality of particulate structures, each of said plurality of particulate structures consisting of poly(glycerol sebacate) (PGS), cerivastatin and everolimus, said cerivastatin is present in an amount of 0.01 wt. % to 0.1 wt. % of said ECM-mimicking composition, said everolimus is present in an amount of 0.001 wt. % to 0.01 wt. % of said ECM-mimicking composition,
   wherein said plurality of particulate structures are adapted to modulate inflammation of damaged cardiovascular tissue in vivo by increasing expression of Kruppel like factor 2 (KLF-2), whereby localized expression of monocyte chemoattractant protein 1 (MCP-1) and C-C chemokine receptor type 2 (CCR2) is inhibited at transcriptional and translational levels as a function of said increased expression of said KLF-2.

* * * * *